United States Patent [19]
Gupta et al.

[11] Patent Number: 6,166,270
[45] Date of Patent: Dec. 26, 2000

[54] EXTRACTIVE DISTILLATION SEPARATION

[75] Inventors: Vijai P. Gupta, Berwyn; Michael J. Szady, Boothwyn, both of Pa.

[73] Assignee: Arco Chemical Technology, L.P., Greenville, Del.

[21] Appl. No.: 09/347,945

[22] Filed: Jul. 6, 1999

[51] Int. Cl.[7] .................................................. C07C 27/02
[52] U.S. Cl. ............................ 568/877; 203/69; 203/70; 568/913
[58] Field of Search .................................. 568/877, 913; 203/69, 70

[56] References Cited

U.S. PATENT DOCUMENTS

| | | |
|---|---|---|
| 2,671,332 | 5/1954 | Cottle et al. . |
| 3,031,495 | 4/1962 | Young et al. . |
| 3,172,905 | 3/1965 | Eckert . |
| 3,173,943 | 3/1965 | Hess et al. . |
| 3,678,099 | 7/1972 | Kemp . |
| 4,473,444 | 9/1984 | Hoyt .......................................... 203/69 |
| 4,525,245 | 6/1985 | Berg .......................................... 203/51 |
| 4,666,650 | 5/1987 | Berg .......................................... 203/57 |
| 4,670,106 | 6/1987 | Berg .......................................... 203/51 |
| 4,675,080 | 6/1987 | Berg .......................................... 203/60 |
| 4,698,137 | 10/1987 | Berg .......................................... 203/51 |
| 4,718,987 | 1/1988 | Berg .......................................... 203/51 |
| 4,718,988 | 1/1988 | Berg .......................................... 203/51 |
| 4,826,576 | 5/1989 | Berg .......................................... 203/56 |
| 5,866,714 | 2/1999 | Szady ....................................... 560/247 |
| 6,018,076 | 1/2000 | Szady ....................................... 560/247 |

*Primary Examiner*—Michael L. Shippen
*Attorney, Agent, or Firm*—Dennis M. Kozak; William C. Long

[57] ABSTRACT

High purity tertiary butyl alcohol is obtained from mixtures comprised of tertiary butyl alcohol and tertiary butyl acetate by extractive distillation using a hydrocarbon extractive solvent such as decane.

5 Claims, 4 Drawing Sheets

EXTRACTIVE DISTILLATION SEPARATION

BACKGROUND OF THE INVENTION

1. Field of the Invention

The present invention relates to the separation of mixtures of tertiary butyl alcohol and tertiary butyl acetate by extractive distillation using a hydrocarbon such as n-decane as solvent.

2. Description of the Prior Art

Tertiary butyl acetate is an important chemical of commerce having wide utility, for example, as a solvent.

It is known to produce tertiary butyl acetate by reaction of acetic acid and isobutylene over a solid sulfonate group containing cation exchange resin. See, for example, U.S. Pat. No. 3,678,099 and references disclosed therein including U.S. Pat. Nos. 2,671,332, 3,031,495, 3,172,905 and 3,173,943.

A significant advance in this art is that described and claimed in copending application Ser. No. 08/816,704 filed Mar. 13, 1997, now abandoned, wherein the reaction between isobutylene and acetic acid is carried out in the presence of tertiary butyl alcohol as selectivity enhancing modifier. See also copending application Ser. No. 09/030,171 filed Feb. 25, 1998, now U.S. Pat. No. 6,018,076, wherein at least part of the selectivity enhancing tertiary butyl alcohol is formed in situ by addition of water to the reaction system.

There is produced in processes such as above described a mixture comprised of tertiary butyl alcohol and tertiary butyl acetate which cannot be resolved by ordinary distillation procedures.

BRIEF DESCRIPTION OF THE INVENTION

In accordance with the present invention, mixtures comprised of tertiary butyl alcohol and tertiary butyl acetate are resolved by extractive distillation using a solvent hydrocarbon such as n-decane.

DETAILED DESCRIPTION

The present invention provides a method for the effective and convenient separation of mixtures comprised of tertiary butyl alcohol and tertiary butyl acetate, especially mixtures which are obtained from processes such as described in copending application Ser. No. 08/816,704 filed Mar. 13, 1997, now abandoned.

Figure 1:
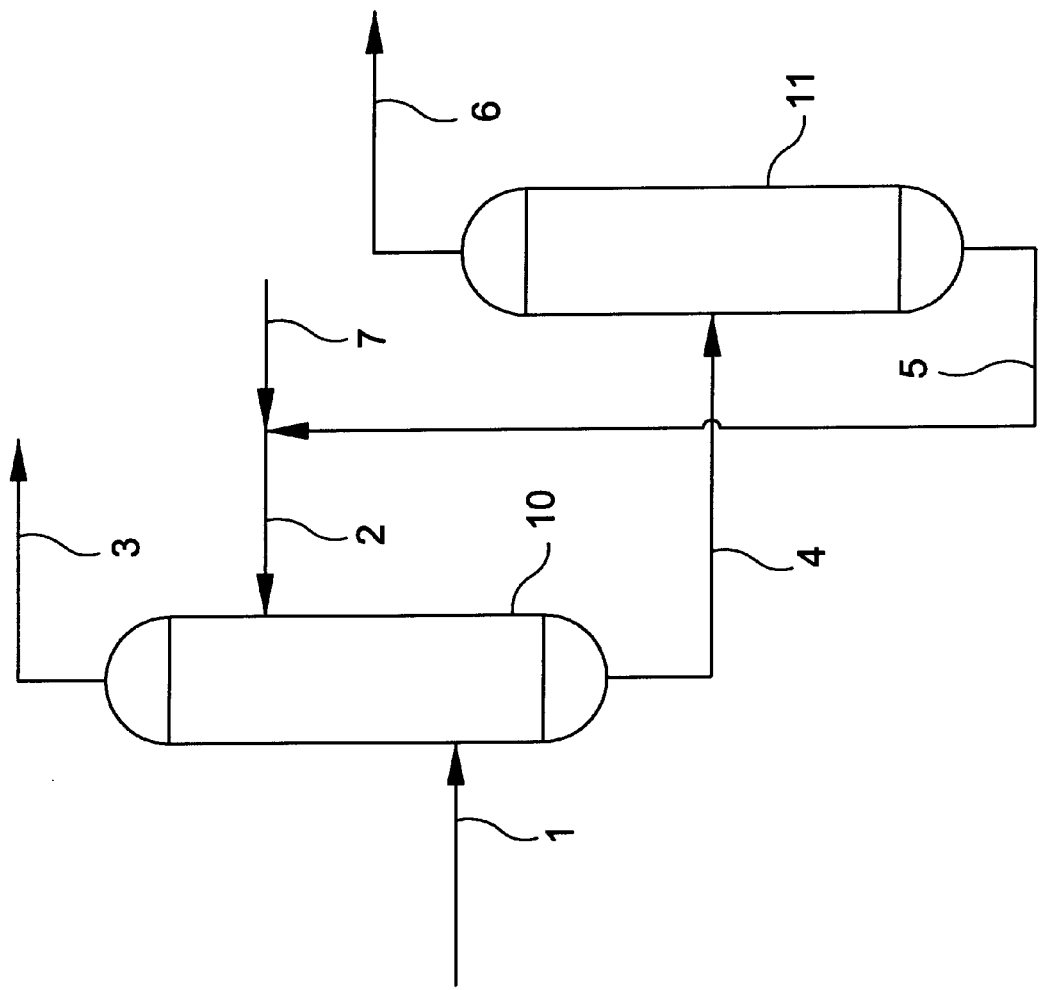
FIG. 1 illustrates practice of the invention.

Referring to FIG. 1, the mixture of tertiary butyl alcohol and tertiary butyl acetate is fed via line 1 to distillation column 10 at an intermediate point and the extractive distillation hydrocarbon solvent is fed to column 10 via line 2 at an upper point. The solvent effectively increases tertiary butyl alcohol volatility relative to tertiary butyl acetate and a tertiary butyl alcohol stream greatly reduced in tertiary butyl acetate content is separated overhead via line 3. The bottoms stream comprised of solvent, tertiary butyl acetate and some tertiary butyl alcohol is removed via 4 and passes to distillation column 11 wherein a tertiary butyl acetate stream containing some tertiary butyl alcohol is stripped overhead and removed via line 6; this stream is conveniently recycled to the tertiary butyl acetate production process. Solvent, substantially free of tertiary butyl acetate and tertiary butyl alcohol is removed as bottoms via line 5 and is conveniently recycled to column 10; make-up solvent is added, as needed, via line 7.

The extractive distillation solvent employed in the instant invention is an aromatic or a linear or branched parafin which is higher boiling than tertiary butyl acetate, preferably at least 5° C. higher boiling and more preferably at least 20° C. higher boiling. Especially suitable are $C_9$–$C_{20}$ aromatic or parafin hydrobarbons, $C_{10}$–$C_{12}$ alkanes being especially preferred.

The tertiary butyl alcohol/tertiary butyl acetate mixtures which are separated in accordance with the invention generally comprise tertiary butyl alcohol and tertiary butyl acetate in a weight ratio of 1/10–10/1. Generally, at least 0.5–20 volumes of solvent are used per volume of tertiary butyl alcohol/tertiary butyl acetate feed.

Figure 2:
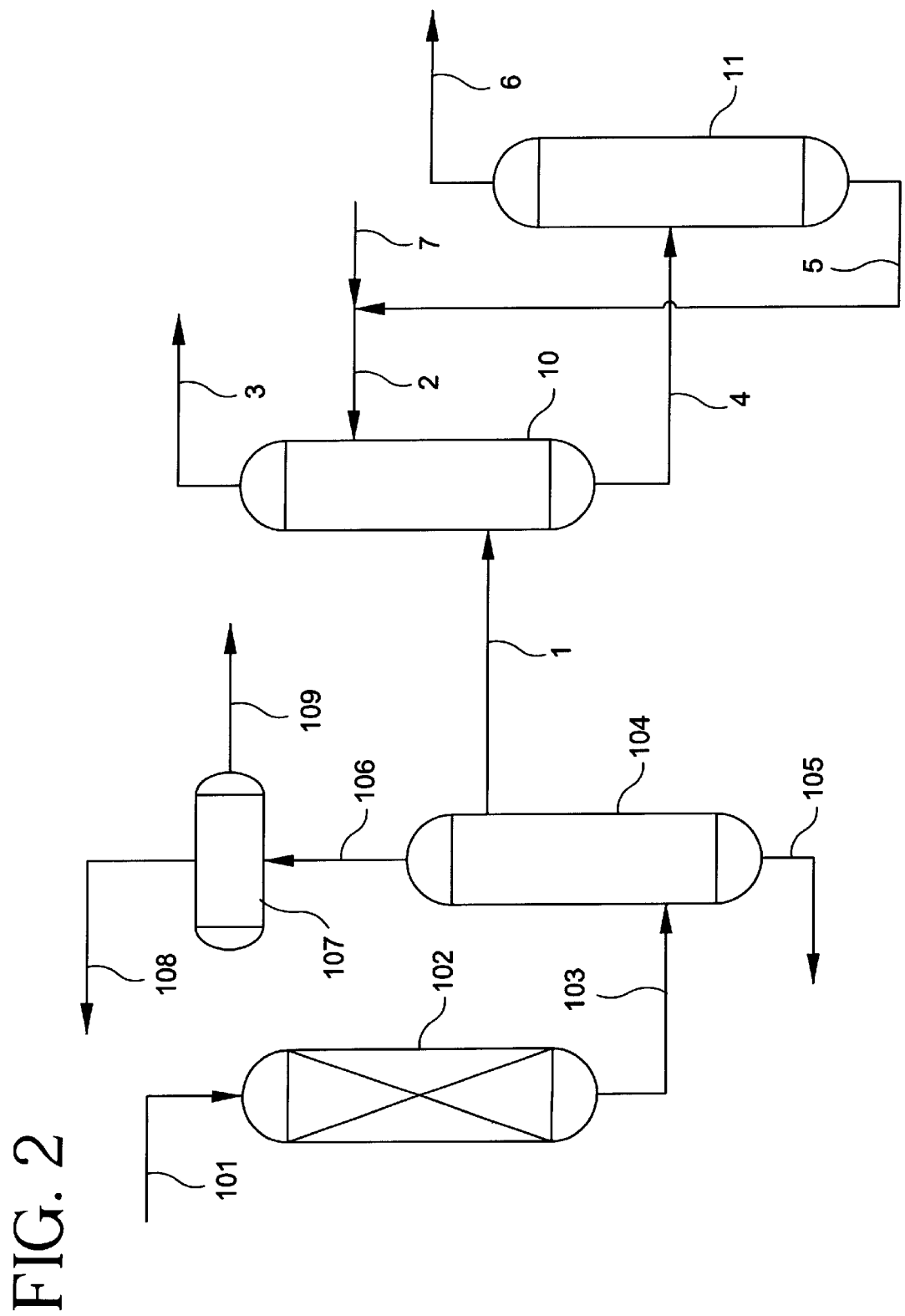
FIG. 2 illustrates an embodiment of the invention wherein prior to the extractive distillation the amount of tertiary butyl acetate in the feed is reduced by a hydrolysis step.

While the invention is illustrated generally in FIG. 1, the embodiment illustrated in FIG. 2 shows an especially advantageous practice wherein the amount of tertiary butyl acetate in the mixture to be fed to the extractive distillation is substantially reduced by a reversion step before the extractive distillation thus significantly reducing solvent requirements during the distillation.

Referring to FIG. 2 a tertiary butyl alcohol recycle stream from a tertiary butyl acetate process, wherein some isobutylene and water are reacted to form tertiary butyl alcohol modifier for the reaction of isobutylene and acetic acid, comprises the feed stream. Illustratively this feed stream is predominantly tertiary butyl alcohol (50% or more by weight) and contains about 5–30 wt % tertiary butyl acetate along with small amounts of water and diisobutylene.

The feed stream passes via line 101 to packed tower reactor 102 which is packed with solid acidic catalyst such as Amberlyst A-15 or similar material including medium and large pore zeolites such as ZSM-5 and zeolite beta, acidic clays, heteropolyacids, and the like. In reactor 102 the feed is reacted at 20–150° C. preferably 50–150° C. and most preferably 80–150° C. to convert tertiary butyl acetate to isobutylene and acetic acid.

The reaction mixture, substantially reduced in tertiary butyl acetate content, exits reactor 102 via line 103 and passes to distillation column 104 wherein impurities are removed. Acetic acid formed in reactor 102 is removed as bottoms via line 105, and this stream can be conveniently recycled to tertiary butyl acetate production. Overhead lights are removed via line 106 and pass to separator 107 with isobutylene passing via line 108 for recycle to tertiary butyl acetate production. A diisobutylene purge is removed via line 109.

The tertiary butyl alcohol and tertiary butyl acetate mixture, now significantly reduced in tertiary butyl acetate content compared with the feed stream in 101 passes via line 1 to extractive distillation column 10 where, as described above in connection with FIG. 1, tertiary butyl alcohol is recovered overhead via line 3 and solvent is recovered as bottoms from column 11.

Figure 3:
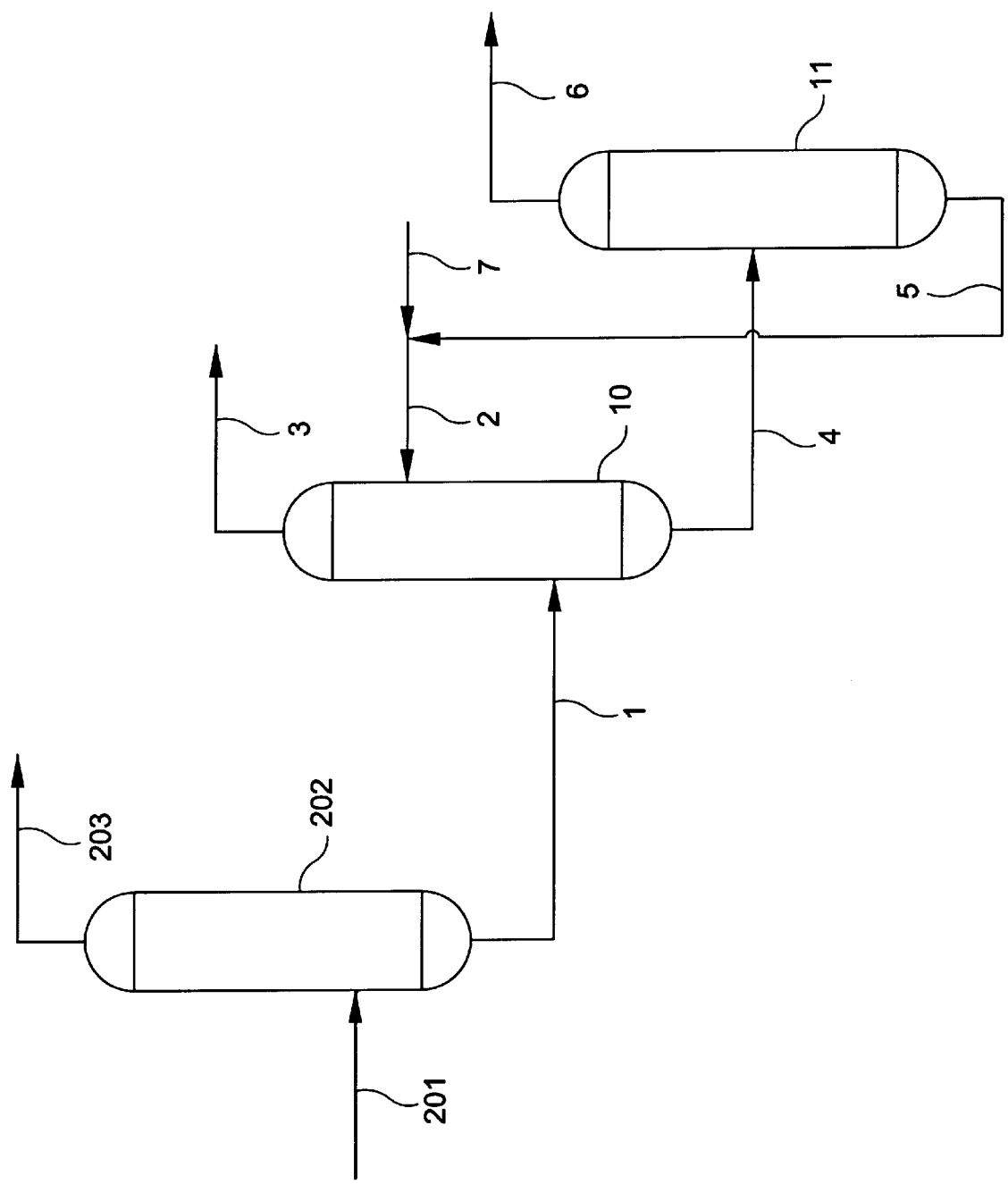
FIG. 3 illustrates an embodiment of the invention wherein prior to the extractive distillation diisobutylene and water are removed in a predistillation step.

FIG. 3 illustrates a practice of the invention wherein the feed is a recycle stream from tertiary butyl acetate production which contains small amounts of water and diisobutylene in addition to tertiary butyl alcohol and tertiary butyl acetate. In this embodiment, the feed passes via line 201 to distillation column 202 from which the water and diisobutylene are separated as their azeotrope with tertiary butyl alcohol and tertiary butyl acetate via line 203. The purified tertiary butyl alcohol and tertiary butyl acetate mixture is removed as bottoms and passes via line 1 to extractive distillation column 10 for separation as described above in relation to FIG. 1.

Figure 4:
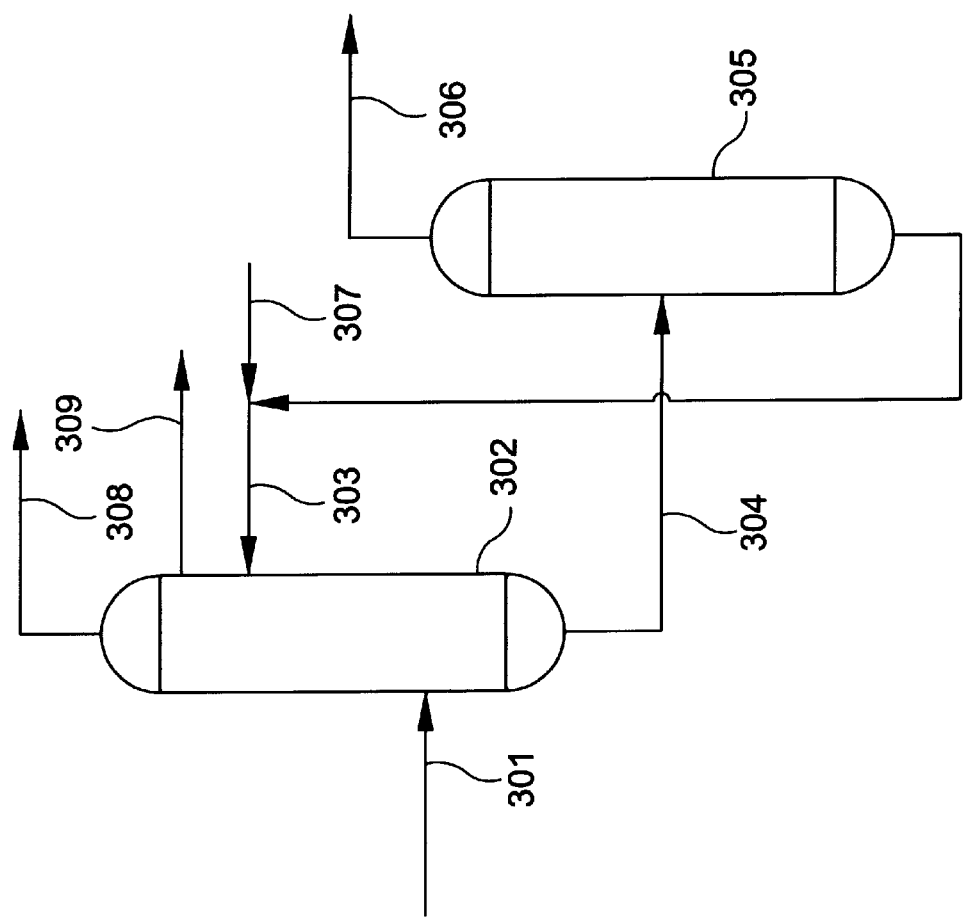
FIG. 4 illustrates an embodiment of the invention wherein water and diisobutylene are contained in the extractive distillation feed, the diisobutylene being separated with the solvent hydrocarbon and the water being separated with tertiary butyl alcohol as an overhead stream.

FIG. 4 represents an alternative to the process of FIG. 3 and also involves a feed stream which contains small amounts of water and diisobutylene in addition to tertiary butyl alcohol and tertiary butyl acetate. In this embodiment the feed passes via line 301 to extractive distillation column 302 with extractive distillation solvent, eg. decane, introduced via line 303. In column 302, the diisobutylene introduced with the feed is removed with the solvent bottoms stream along with tertiary butyl acetate and some tertiary butyl alcohol and passes via line 304 to stripping column 305. In column 305, diisobutylene, tertiary butyl acetate and tertiary butyl alcohol are stripped overhead via line 306 for recycle to tertiary butyl acetate production while solvent is removed as bottoms and recycled to column 302 via line 303. Make up solvent is added as needed via line 307.

In column 302, water will go overhead with tertiary butyl alcohol and a small pasteurization section is provided which takes a water/tertiary butyl alcohol azeotrope overhead via line 308 for recycle to tertiary butyl acetate production. Product tertiary butyl alcohol is withdrawn as a sidestream via line 309.

COMPARATIVE EXAMPLE A

A continuous distillation column is set up with three packed sections each equivalent to a 10 tray Oldershaw column. A feed of 80 wt % tertiary butyl alcohol and 20 wt % tertiary butyl acetate is fed to column between the bottom two packed sections at the rate of 300 ml/hr. an overhead product stream was removed at 77–79° C. and atmospheric pressure, the composition of which was roughly independent of reflux ratio and which was in the range of 89–92 wt % tertiary butyl alcohol.

This example established that tertiary butyl alcohol and tertiary butyl acetate mixtures cannot be satisfactorily distilled by conventional procedures to produce high purity tertiary butyl alcohol.

Example 1

The same continuous distillation column and feed composition as in comparative Example A was employed. The extractive distillation solvent was n-decane which was fed between the top two packed sections.

Feed tertiary butyl alcohol/tertiary butyl acetate stream was fed at the rate of 95 ml/hr and solvent feed rate was 370 ml/hr. At a reflux ratio of 5/1, a high purity tertiary butyl alcohol stream was removed overhead at 80° C. and atmospheric pressure at a flow rate of 50 ml/hr. The composition of the overhead by weight was 99.6% tertiary butyl alcohol and 0.4% tertiary butyl acetate. A bottoms stream at 107° C. and 20 psia was removed at the rate of 405 ml/hr, the composition by weight being 11.3% tertiary butyl alcohol, 4.0% tertiary butyl acetate, and 84.7% decane.

Upon increasing the reflux ratio to 10/1, the tertiary butyl alcohol purity in the overhead increased to 99.7 wt %. The flow rate, however, was reduced by 30%.

COMPARATIVE EXAMPLE B

The same distillation column and feed composition was used as Example 1. Propylene glycol extractive distillation solvent was employed.

The tertiary butyl alcohol/tertiary butyl acetate feed rate was 200 ml/hr and the propylene glycol feed rate was 100 ml/hr. With a 4/1 reflux ratio the overhead flow rate was 30 ml/hr and the composition by weight was 90.7% tertiary butyl alcohol, and 9.3% tertiary butyl acetate. Bottoms flow rate was 290 ml/hr and the composition by weight was 56.2% tertiary butyl alcohol, 13.4% tertiary butyl acetate and 30.4% propylene glycol.

Comparative Example A presented above demonstrates that high purity tertiary butyl alcohol cannot be obtained by conventional distillation.

Comparative Example B demonstrates that high purity tertiary butyl alcohol cannot be obtained by extractive distillation using polar solvent such as propylene glycol. Example 1 demonstrates the outstanding results achieved in accordance with the invention.

Example 2

The example illustrates the process of FIG. 2. About 750 ml of a tertiary butyl alcohol recycle stream containing 80.1 wt % tertiary butyl alcohol, 18.3 wt % tertiary butyl acetate, 1.2 wt % water and 0.5 wt % diisobutylene was fed to a batch reactor which contained 10 grams of Amberlyst A-15 resin. The mixture was maintained at 80° C. and 50 psig for 4 hours at which time the mixture contained only 2.8 wt % tertiary butyl acetate as a result of conversion of the tertiary butyl acetate to isobutylene and acetic acid.

The reaction mixture was distilled to separate impurities overhead and acetic acid as bottoms. An intermediate tertiary butyl alcohol and tertiary butyl acetate stream is distilled as described in Example 1 to recover high purity tertiary butyl alcohol.

Solvent requirements were greatly reduced as a result of the preconversion of tertiary butyl acetate to acetic acid and isobutylene.

Example 3

This example illustrates practice of the process of FIG. 3. Referring to FIG. 3, the same feed mixture as was employed in Example 2 was fed via line 201 to distillation column 202. An overhead stream is removed via line 203 at 76° C. and atmospheric pressure comprising the water and diisobutylene azeotrope with tertiary butyl alcohol and tertiary butyl acetate and having the composition 62.5 wt % tertiary butyl alcohol, 12.5 wt % tertiary butyl acetate, 12.5 wt % water and 12.5 wt % diisobutylene.

The bottoms tertiary butyl alcohol and tertiary butyl acetate is fed via line 1 and extractively distilled as described in Example 1.

Example 4

Referring to FIG. 4, as an alternative to the process of Example 3 the same feed used in Examples 2 and 3 is fed via line 301 to extractive distillation column 302, with n-decane extractive distillation solvent fed via line 303.

A water/tertiary butyl alcohol azeotrope is removed overhead via line 308 at 79° C. and atmospheric pressure. High purity product tertiary butyl alcohol is withdrawn as a sidestream via line 309 at 82° C. and atmospheric pressure.

Bottoms comprised of solvent n-decane, diisobutylene together with some tertiary butyl alcohol and tertiary butyl acetate is removed as bottoms via line 304 and passes to stripper 305. In the stripper, diisobutylene tertiary butyl alcohol and tertiary butyl acetate are stripped overhead at 98° C. and atmospheric pressure and may be recycled to tertiary butyl acetate production. Solvent n-decane passes via 303 back to column 302, make-up solvent is added as needed via line 307.

We claim:

1. The process for separating tertiary butyl alcohol from a feed mixture comprised of tertiary butyl alcohol and tertiary butyl acetate which comprises extractive distillation of the mixture using a $C_9$–$C_{20}$ aromatic or paraffinic hydrocarbon extractive distillation solvent.

2. The process of claim 1 wherein the solvent is n-decane.

3. The process of claim 1 wherein the tertiary butyl acetate content of the feed mixture is reduced by reaction over an acidic catalyst prior to extractive distillation.

4. The process of claim 1 wherein water and diisobutylene are separated as the azeotrope with tertiary butyl alcohol and tertiary butyl acetate prior to extractive distillation.

5. The process of claim 1 wherein the solvent is a mixture of $C_9$–$C_{12}$ paraffin hydrocarbons.

* * * * *